(12) United States Patent
Xie et al.

(10) Patent No.: US 12,306,134 B2
(45) Date of Patent: May 20, 2025

(54) METHODS, APPARATUSES, AND SYSTEMS PROVIDING DEHUMIDIFICATION FOR GAS DETECTING COMPONENTS

(71) Applicant: Honeywell International Inc., Charlotte, NC (US)

(72) Inventors: Guangli Xie, Charlotte, NC (US); Jing Wei, Charlotte, NC (US); Xiaolin Tian, Charlotte, NC (US); Wei Yu, Charlotte, NC (US); Zhongliang Meng, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 840 days.

(21) Appl. No.: 17/452,938

(22) Filed: Oct. 29, 2021

(65) Prior Publication Data

US 2022/0170886 A1 Jun. 2, 2022

(30) Foreign Application Priority Data

Nov. 30, 2020 (CN) .......................... 202011370215.4

(51) Int. Cl.
| | | |
|---|---|---|
| *B01D 53/02* | (2006.01) | |
| *G01N 1/42* | (2006.01) | |
| *G01N 27/66* | (2006.01) | |
| *G01N 33/00* | (2006.01) | |
| *B01D 53/26* | (2006.01) | |

(52) U.S. Cl.
CPC ............... *G01N 27/66* (2013.01); *G01N 1/42* (2013.01); *G01N 33/0047* (2013.01); *B01D 53/26* (2013.01)

(58) Field of Classification Search
CPC .......... B01D 53/26; G01N 1/42; G01N 27/66; G01N 33/004; G01N 33/0047
See application file for complete search history.

(56) References Cited

U.S. PATENT DOCUMENTS

| 5,115,666 A | 5/1992 | Williams |
| 2009/0064698 A1* | 3/2009 | Spanger ................ F24F 13/222 62/289 |
| 2018/0030695 A1* | 2/2018 | Ng ............................ E03B 3/28 |
| 2021/0104140 A1* | 4/2021 | Park ..................... G08B 17/117 |

OTHER PUBLICATIONS

Decision to grant a European patent Mailed on Aug. 1, 2024 for EP Application No. 21205398, 2 page(s).
Intention to grant Mailed on Mar. 22, 2024 for EP Application No. 21205398, 9 page(s).
European Search Report and Search Opinion received for EP Application No. 21205398.7, mailed on Mar. 31, 2022, 8 pages.
European search report Mailed on Oct. 18, 2024 for EP Application No. 24192671, 9 page(s).

* cited by examiner

*Primary Examiner* — Christopher P Jones
(74) *Attorney, Agent, or Firm* — Alston & Bird LLP (57) ABSTRACT

Methods, apparatuses and systems for providing dehumidification providing dehumidification for gas detecting components are disclosed herein. An example apparatus may comprise: a humidity sensing component configured to generate a humidity level indication associated with gaseous substance in a gas flow channel, a dehumidifier component disposed along the gas flow channel, a gas detecting component disposed downstream with respect to the dehumidifier component along the gas flow channel, and a controller component in electronic communication with the humidity sensing component and the dehumidifier component.

16 Claims, 7 Drawing Sheets

METHODS, APPARATUSES, AND SYSTEMS PROVIDING DEHUMIDIFICATION FOR GAS DETECTING COMPONENTS

CROSS-REFERENCE TO RELATED APPLICATIONS

This application claims priority pursuant to 35 U.S.C. 119(a) to China Patent Application No. 202011370215.4, filed Nov. 30, 2020, which application is incorporated herein by reference in its entirety.

BACKGROUND

Gas detectors may detect and/or measure the concentration level of gaseous substance and/or compounds in a gaseous substance, including, for example, organic compounds and inorganic compounds. Many gas detectors are plagued by technical challenges and limitations. For example, when the gaseous substance comprises a significant amount of water vapor, many gas detectors fail to produce accurate readings.

BRIEF SUMMARY

Various embodiments described herein relate to methods, apparatuses, and systems for providing dehumidification for an apparatus such as, for example, a photoionization detector.

In accordance with various examples of the present disclosure, an apparatus is provided. The apparatus may comprise: a humidity sensing component configured to generate a humidity level indication associated with gaseous substance in a gas flow channel, a dehumidifier component disposed along the gas flow channel, a gas detecting component disposed downstream with respect to the dehumidifier component along the gas flow channel and a controller component in electronic communication with the humidity sensing component and the dehumidifier component.

In some examples, the controller component is configured to: receive the humidity level indication from the humidity sensing component, determine whether the humidity level indication satisfies a humidity level threshold and in response to determining that the humidity level indication satisfies the humidity level threshold, transmit a first control indication to trigger activating the dehumidifier component.

In some examples, the controller component is configured to: in response to determining that the humidity level indication does not satisfy the humidity level threshold, transmit a second control indication to trigger deactivating the dehumidifier component.

In some examples, the humidity level threshold is between 40% and 60% relative humidity.

In some examples, the dehumidifier component comprises a cooling element in contact with the gaseous substance in the gas flow channel.

In some examples, the dehumidifier component comprises a filter component disposed underneath the cooling element, wherein the filter component is disposed in the gas flow channel, and wherein the gas flow channel intersects at least a portion of a water channel.

In some examples, the gaseous substance in the gas flow channel comprises water vapor, wherein, when activating the dehumidifier component, the controller component is configured to further activate the cooling element, wherein the cooling element is configured to decrease a temperature level in the gas flow channel, causing the water vapor to condense on a surface of the filter component.

In some examples, the filter component comprises one or more metal net structures arranged within the gas flow channel, wherein the gaseous substance flows through the one or more metal net structures.

In some examples, the dehumidifier component further comprises a water absorbing material arranged underneath the filter component, wherein the water absorbing material is disposed in the water channel and is configured to absorb a liquid substance from a surface of the filter component.

In some examples, the apparatus further comprises a pump, and wherein the water absorbing material is further configured to, in conjunction with output air of the pump, expel the water vapor from the apparatus.

In some examples, the water absorbing material comprises a foam or a textile.

In accordance with various examples of the present disclosure, a method is provided. The method may comprise receiving, by a controller component, a humidity level indication from a humidity sensing component, determining, by the controller component, whether the humidity level indication satisfies a humidity level threshold and in response to determining that the humidity level indication satisfies the humidity level threshold, transmit a first control indication to trigger activating a dehumidifier component.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such components or features may be optionally included in some embodiments, or may be excluded.

The term "electronically coupled" or "in electronic communication with" in the present disclosure refer to two or more electrical elements (for example, but not limited to, an example processing circuitry, communication module, input/output module memory, humidity sensing component, cooling element, gas detection component) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

Various apparatuses (such as, but not limited to, a photoionization detector) may measure the concentration level of volatile organic compounds in a gaseous substance. The term "volatile organic compound" (or "VOC") refers to organic compounds that may have a high vapor pressure at ordinary room temperature (i.e., they may easily become gases or vapors). Example chemicals in example VOCs may include, for example, but not limited to, formaldehyde, methane, and benzene. A high-level concentration of VOCs in a gaseous substance (for example, indoor air or outdoor air) may cause adverse effect on health and environment. As such, photoionization detectors may be utilized to measure and monitor the concentration level of VOCs in various indoor and/or outdoor locations.

In some examples, a photoionization detector may be implemented in humid environments to detect the concentration level of VOC. The water vapor in such environment may cause various technical problems and difficulties. For example, the water vapor may cause the photoionization detector to malfunction and/or may cause the photoionization detector to produce inaccurate readings.

Figure 1:
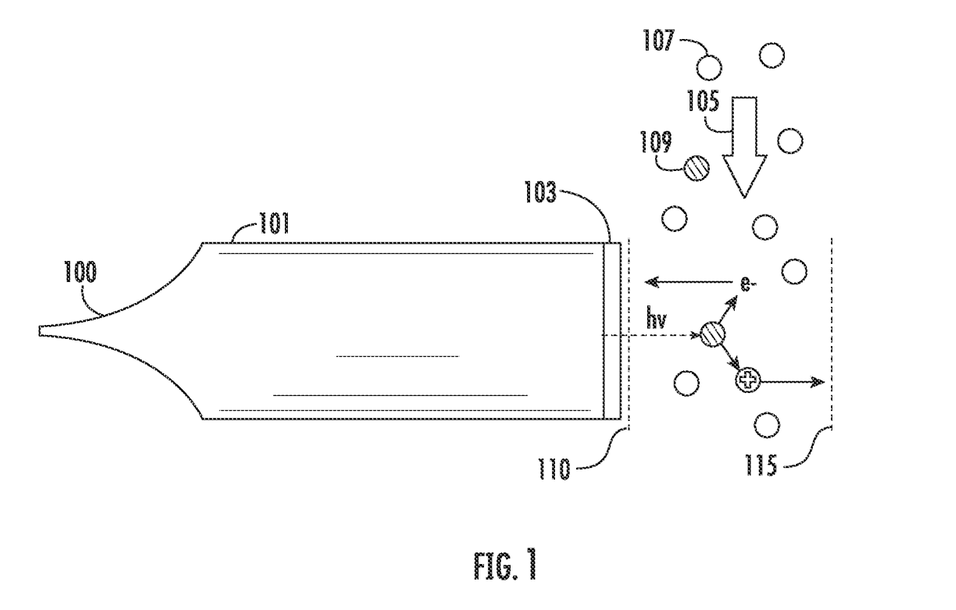
FIG. 1 illustrates an example portion of an example apparatus in accordance with various embodiments of the present disclosure.

Referring now to FIG. 1, an example schematic diagram depicts an example photoionization lamp 100 of an example gas detecting component (for example, an example photoionization detector) in accordance with various embodiments of the present disclosure. In particular, the example photoionization lamp 100 may comprise a glass tube member 101 and a window member 103.

As depicted in FIG. 1, the glass tube member 101 may comprise a gaseous substance or a combination of gaseous substances, which may include but are not limited to, inert gases such as argon (Ar), xenon (Xe), and/or krypton (Kr). The gaseous substance(s) within the glass tube member 101 may be excited through any of a variety of excitation methods to produce an ultraviolet (UV) light source. For example, a voltage (e.g., an alternating current (AC) voltage) may be supplied to the glass tube member 101. In such examples, the AC voltage may cause ionization of the gaseous substance(s) within the glass tube member 101, resulting in a glow discharge. The glow discharge associated with the plasma may emit a low-wavelength ultraviolet (UV) light. Ultraviolet light may be transmitted through the window member 103. In some examples, the window member 103 may comprise material(s) that enable and/or facilitate transmission of low-wavelength ultraviolet light, including, for example, salt crystal materials. As the ultraviolet light passes through the window member 103, molecules in a gaseous substance may be exposed to the ultraviolet light and detected by the example gas detecting component (for example, an example photoionization detector).

In particular, the example gas detecting component (for example, an example photoionization detector) may be configured to detect a testing compound in a testing gaseous substance (for example but not limited to, VOC(s) in the air). In some embodiments, the example gas detecting component (for example, an example photoionization detector) may comprise an anode element (e.g., bias electrode 110) and a cathode element (e.g., signal electrode 115). In some examples, the anode element may be an electrode that attracts negatively charged electrons. In some examples, the cathode element may be an electrode that attracts positively charged electrons.

As shown in FIG. 1, the testing gaseous substance (such as air) may flow through the example gas detecting component (for example, an example photoionization detector) in a direction as indicated by arrow 105. The testing gaseous substance may comprise VOC molecules 109 and non-VOC molecules 107. As VOC molecules 109 and non-VOC molecules 107 pass by the photoionization lamp 100, they may be exposed to the ultraviolet light generated by the photoionization lamp 100. In the example shown in FIG. 1, the ultraviolet light may cause photoionization of the VOC molecules 109. The term "photoionization" may refer to an occurrence when an atom/molecule absorbs light, which at sufficient levels causes an electron to leave, creating a positive ion. Ions produced during this process are collected on electrodes, generating electric current.

In the example shown in FIG. 1, the photoionization of the VOC molecules 109 may result in electrons of the VOC molecules 109 being ejected and forming positively charged ions. The electrons may travel to the anode element (e.g., bias electrode 110), while the positively charged ions may travel to the cathode element (e.g., signal electrode 115). As the electrons and the positively charged ions are propelled to the corresponding electrodes, an electric current may be generated. In contrast, the ultraviolet light may not cause photoionization of the non-VOC molecules (e.g., non-VOC air) 107 and, as a result, the non-VOC molecules 107 do not generate electric current.

In some embodiments, the electric current generated may be proportional to the amount of testing compound in a testing gaseous substance (for example but not limited to, VOC(s) in the air). As such, the example gas detecting component (for example, an example photoionization detector) may provide a measure of the concentration level of the testing compound. For example, the example gas detecting component (for example, an example photoionization detector) may measure the electric current and convert this measure to a concentration level of VOCs present in the air.

In the example shown in FIG. 1, the electric current generated through the photoionization caused by the ultraviolet light from the photoionization lamp 100 is proportional to the amount of VOC molecules 109 in the air. As such, the concentration level of the VOCs may be determined based at least in part on the electric current that is generated through the photoionization.

As described above, many photoionization detectors may receive a gaseous substance that may comprise water vapor. The level/amount of the water vapor in the gaseous substance may be represented as absolute humidity (AH) or relative humidity (RH). The term absolute humidity may refer to a measure of the total mass of water vapor in a particular volume or mass of a gaseous substance, which is not dependent on a corresponding temperature. Absolute humidity may be expressed as grams of moisture per cubic meter of air (g/m$^3$). For example the absolute humidity of air at 0° C./32° F. is approximately 5 g/m$^3$. Absolute humidity can be expressed in accordance with the following equation:

$$AH = \frac{mH2O}{Vnet}$$

Where:
AH=absolute humidity (g/m$^3$);
mH$_2$O=mass of water vapor (g); and
V$_{net}$=volume of gaseous substance (e.g., air and water vapor mixture) (g/m$^3$).

The term relative humidity may refer to a ratio of a partial pressure of water vapor (e.g., actual vapor pressure) to an equilibrium vapor pressure of water (e.g., saturated pressure of water) at a particular temperature. Accordingly, the same amount of water vapor corresponds with a higher relative humidity at lower temperatures in comparison to higher temperatures. Relative humidity may be expressed in accordance with the following equation:

$$\varphi = \frac{\rho w}{\rho ws} * 100\%$$

Where:
$\varphi$=relative humidity (%);
$\rho_w$=vapor density (kg/m$^3$); and
$\rho_{ws}$=vapor density at saturation at actual dry bulb temperature (kg/m$^3$).

As an example, if a particular air sample holds 30 grams of water vapor and can hold a maximum of 50 grams of water vapor, then the relative humidity can be expressed as $$\frac{30}{50},$$

or 60% relative humidity.

As described above, the presence of water vapor in a gaseous substance may cause many technical challenges and limitations.

As an example, gas detection components (e.g., photoionization detector) may be calibrated using a calibration gaseous substance, and then be utilized to generate measurements indicating a concentration level of a testing compound in a testing gaseous substance (for example, the concentration level of VOC in ambient air).

In some embodiments, the calibration gaseous substance may have a humidity level (for example, AH and/or RH) that is different from the humidity level (for example, AH and/or RH) of the testing gaseous substance. For example, the calibration gaseous substance may not comprise water vapor (e.g. a "dry" calibration gas substance), while the testing gaseous substance may have various degrees of water vapor (e.g., varying values of humidity levels). As an example, water vapor may be ubiquitous in testing gaseous substance such as ambient air. The discrepancy in the humidity level between the calibration gaseous substance and the testing gaseous substance may reduce responsiveness of gas detection components (e.g., photoionization detectors) and may increase measurement error rates in gas detection components (e.g., photoionization detectors). For example, when the testing gaseous substance is associated with a high humidity level (such as, but not limited to, 95% RH), the responsiveness of gas detection components (e.g., photoionization detectors) may be reduced by over 50% as compared to the responsiveness when the testing gaseous substance is associated with a lower humidity level conditions (e.g., a "dry" testing gaseous substance that does not comprise water vapor). In some embodiments, if the humidity level of a testing gaseous substance is below 50% RH, the measurement error rate in gas detection components (e.g., photoionization detectors) may likely be less than 20%.

As noted above, during operations, a testing gaseous substance (e.g., comprising a combination of VOC and non-VOC molecules) may come in contact with a gas detection component for testing. In some embodiments, the testing gaseous substance may have a high humidity level and therefore also have a corresponding large amount of water vapor therein (e.g., as indicated by a measured AH and/or RH value). During testing, if a testing gaseous substance comprising a large proportion of water vapor comes in contact with the gas detection component, some of the water vapor may condense onto the gas detection component (e.g., photoionization detector) and cause an increase in the amount of electric current that is generated (e.g., between the bias electrode 110 and the signal electrode 115). In other words, the presence water vapor in a testing gaseous substance may result in a false positive current being generated (e.g., false positive "leak" current). Accordingly, high humidity environments may provide testing gaseous substances with large amounts of water vapor and result in inaccurate electric current measurements by the gas detection component, such as between the signal electrode 115 and the bias electrode 110.

In another example, in order for a gas detection component (e.g., photoionization detector) to function optimally, its surfaces should be kept free of dust. As noted above, a particular testing gaseous substance may be associated with a particular humidity level and corresponding amount of water vapor therein. As a gaseous substance is conveyed to a gas detection component, some of the water vapor present may absorb dust particles in ambient air before reaching the gas detection component and in some cases may deposit the dust particles thereon. During operations, when a testing gaseous substance with a relatively low humidity level that is within an optimal range (e.g., between 40% and 60% RH) is conveyed to a gas detection component (e.g., photoionization detector), a smaller overall amount of water vapor will make contact with the gas detection component (e.g., photoionization detector) and thus it is less likely that dust particles will be deposited onto the gas detection component. However, when a testing gaseous substance associated with a high humidity level and corresponding large amount of water vapor is conveyed to a gas detection component (e.g., photoionization detector), the amount of water vapor present may be substantial such that minute and invisible dust or dirt particles absorbed by the water vapor may reach the gas detecting component (e.g., photoionization detector) and be deposited thereon. As a result of such unwanted deposits, which may accumulate as the gas detection component is used over time, the sensitivity and performance of the gas detection component may be negatively affected. By way of example, the output UV light generated by an example photoionization lamp which is proportional to the amount of VOC molecules in the air may be weakened due to the presence of dust resulting in reduced sensitivity of the gas detection component. Additionally, having to maintain or frequently clean a gas detecting component increases maintenance costs and labor for an end user.

In accordance with various embodiments of the present disclosure, example methods, apparatuses and systems are provided.

For example, the present disclosure may provide an apparatus configured to receive a gaseous substance and convey the gaseous substance from a gas inlet through a gas flow channel to be expelled from the apparatus (e.g., caused to exit the apparatus) via a gas outlet. The example apparatus may comprise a humidity sensing component for generating a humidity level indication associated with the gaseous substance in the gas flow channel. The example apparatus may receive a humidity level indication from the humidity sensing component and determine whether the humidity level indication satisfies a humidity level threshold. The term humidity level threshold may refer to a threshold humidity value below which the apparatus can operate at a reduced or acceptable error tolerance. In response to determining that the humidity level indication satisfies the humidity level threshold (e.g., is above the humidity level threshold), the apparatus may transmit a first control indication to trigger activating a dehumidifier component for decreasing a temperature level in the gas flow channel by causing water vapor to condense. In response to determining that the humidity level indication does not satisfy the humidity level threshold (e.g., is equal to or below the humidity level threshold), the apparatus may transmit a second control indication to deactivate the dehumidifier component.

In various embodiments, the humidity level threshold may be a measure of relative humidity or absolute humidity associated with the gaseous substance in the gas flow channel. By way of example, the humidity level threshold may be 60% RH. When the gaseous substance (e.g., humid or damp air) is conveyed along the gas flow channel, it makes contact with and flows through at least a portion of the dehumidifier component. In some embodiments, the dehumidifier component may comprise an arrangement of a plurality of components. In some embodiments, a portion of the dehumidifier may be contained within a vertical water channel. In some embodiments, the dehumidifier component may comprise a cooling element adjacent a top portion of the example vertical water channel, a water absorbing material disposed with and at a bottom portion of the water channel and a filter component therebetween, arranged such that the filter component intersects with at least a portion of the gas flow channel.

For example, the gaseous substance may be conveyed through an arrangement of one or more metal net structures defining the filter component of the dehumidifier component. In some embodiments, a cooling element may be activated to decrease a temperature level in the gas flow channel by causing water vapor to condense. In some embodiments, the water vapor may be caused to condense on a surface of the filter component (e.g., one or more metal net structure(s)), causing reduction of the humidity level of the gaseous substance to fall below the humidity level threshold and therefore within an acceptable range for operations of the apparatus. Additionally, due to the arrangement of the dehumidifier component and gravitational forces acting thereon, the water vapor collected by the filter component may be pulled down and conveyed downward (e.g., along the metal net structure(s)) and may then be absorbed by the water absorbing material. In various embodiments, a pump may pull in (e.g., draw in) a gaseous substance (e.g., input air) through an inlet of the gas flow channel and push the gaseous substance (e.g., output air) through an outlet of the gas flow channel. Thus, output air of the pump which conveys the gaseous substance from an input end to an output end of a gas flow channel may also convey (e.g., push) incident water vapor from a bottom portion of the dehumidifier component (e.g., water absorbing material) along the gas flow channel and expel the water vapor from the apparatus.

While some of the embodiments herein provide an example photoionization detector as an example of gas detection component, it is noted that the scope of the present disclosure is not limited to such embodiments. For example, in some examples, an example gas detection component in accordance with the present disclosure may be in other forms.

Figure 2:
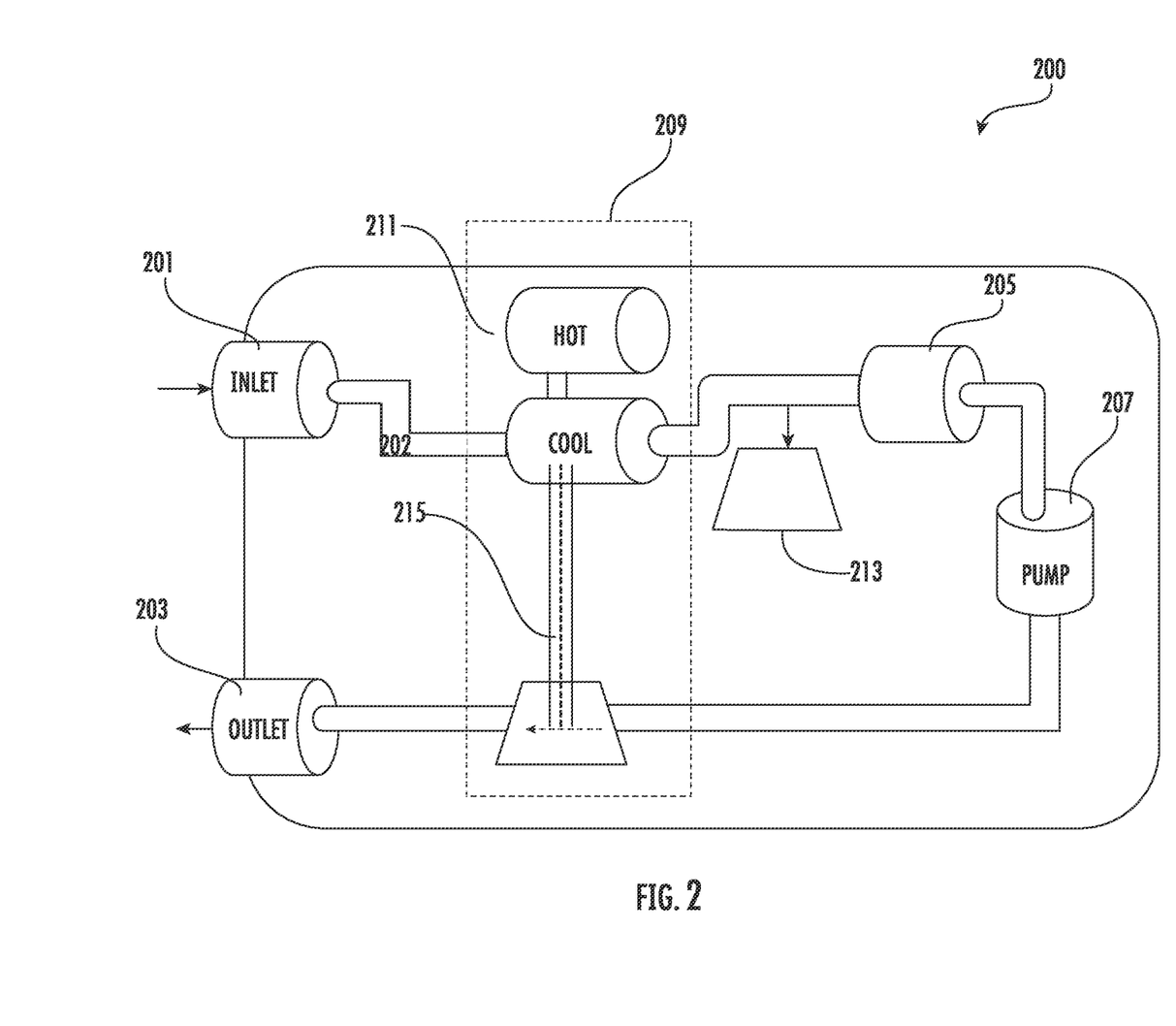
FIG. 2 illustrates an example schematic diagram depicting an apparatus in accordance with various embodiments of the present disclosure.

Referring now to FIG. 2, an example schematic diagram depicting an example apparatus 200 in accordance with various embodiments of the present disclosure is provided. As illustrated, the apparatus 200 comprises a gas flow channel 202, a dehumidifier component 209, a humidity sensing component 213, a gas detecting component 205 and a pump 207.

As depicted, the apparatus 200 contains a gas flow channel 202. The gas flow channel 202 may refer to a passageway beginning with a gas inlet 201 and terminating at a gas outlet 203 through which a gaseous substance (such as, but not limited to, testing gaseous substance that comprises testing compound) may enter, flow through and be expelled from the apparatus 200. The gas flow channel 202 may be or comprise, for example, without limitation, a pipe, conduit, tubular structure and/or the like.

Referring again to FIG. 2, a gaseous substance (for example, a testing gaseous substance) may enter the apparatus 200 through the gas inlet 201. In some embodiments, the gas inlet 201 may refer to an opening on a surface of the housing of the apparatus 200. Similarly, in some embodiments, the gas outlet 203 may refer to an opening on a surface of the housing of the apparatus 200 that may be distinct from the opening on the surface associated with the gas inlet 201. The gas inlet 201 and the gas outlet 203 may be connected by the gas flow channel 202 and define the beginning point and end point of the gas flow channel 202, respectively. In some embodiments, the gaseous substance may be conveyed in a direction due to air flow generated by the pump 207. For example, the pump 207 may generate air flow in the gas flow channel 202 such as by pulling in (e.g., drawing in) a gaseous substance (e.g., input air) through the gas inlet 201 and pushing the gaseous substance (e.g., output air) through the gas outlet 203. Thus, the gaseous substance is received through an opening (e.g., gas inlet 201) leading to the gas flow channel 202 and conveyed to another opening (e.g., gas outlet 203) where it may be expelled from the apparatus 200. In some embodiments, the pump 207 may be or comprise, for example, without limitation a compressor, a vacuum pump, a manual pump, a motorized pump or the like.

Subsequent to entering the apparatus 200 through the gas inlet 201, in some embodiments, the gaseous substance may reach the dehumidifier component 209. In the example shown in FIG. 2, the dehumidifier component 209 may comprise a water channel 215 defining a passage through which water vapor can be expelled from the device without coming in contact with additional components within the apparatus 200, such as the humidity sensing component 213 and the gas detecting component 205. As shown, humidity sensing component 213 and the gas detecting component 205 are each located downstream with respect to the dehumidifier component 209. The term downstream may refer to a location of a first component in a gas flow channel with respect to second component in the gas flow channel, based at least in part on the direction of flow of a gaseous substance within the gas flow channel. For example, if a gaseous substance flows to component A, and subsequently flows to component B, then component B is downstream with respect to component A. Similarly, the term upstream may refer to a location of a first component in a gas flow channel with respect to second component in the gas flow channel, based at least in part on the direction of flow of a gaseous substance within the gas flow channel. For example, if a gaseous substance flows to component A, and subsequently flows to component B, then component A is upstream with respect to component B.

Returning to FIG. 2, subsequent to the water vapor descending downward via the water channel 215, the output air of the pump 207 may push the water vapor from a bottom portion of the dehumidifier component further along the gas flow channel in order to expel the water vapor from the apparatus through the gas outlet 203.

Subsequent to flowing past the dehumidifier component 209, the gaseous substance is conveyed further into the apparatus 200 along the gas flow channel 202 and may reach the humidity sensing component 213, which is also disposed along the gas flow channel 202. As shown, the humidity sensing component 213 is disposed downstream along the gas flow channel with respect to the dehumidifier component 209. Subsequently, the gaseous substance may be conveyed even further within the apparatus 200 along the gas flow channel 202 and may reach the gas detecting component 205. As shown, the gas detecting component 205 may be located downstream with respect to the humidity sensing component 213. Subsequent to reaching (e.g., flowing through) the gas detecting component 205, the gaseous substance may be conveyed along the gas flow channel 202, such as by output air of the pump 207, until it is expelled from the apparatus 200 via the gas outlet 203.

As noted above, the humidity sensing component 213, which is located upstream with respect to the gas detecting component 205, may detect a humidity level associated with the gaseous substance in the gas flow channel 202 and may provide (e.g., transmit) a humidity level indication to the processing circuitry of the apparatus 200. Accordingly, prior to coming into contact with the gas detecting component 205, the processing circuitry of the apparatus may transmit a control indication to trigger activating the dehumidifier component 209. The dehumidifier component 209 may receive the control indication and be activated to decrease a temperature level in the gas flow channel 202, such as by causing water vapor to condense on a filter component or a portion of the dehumidifier component 209. The humidity sensing component 213 may be or comprise a sensor that can detect and measure a moisture level and/or temperature value associated with a gaseous substance. For example, the humidity sensing component 213 can detect and measure temperature, relative humidity (RH), dew point (temperature at which a gaseous substance must be cooled to become saturated with water vapor), absolute humidity (by combining a relative humidity measurement with a temperature measurement), combinations thereof and/or the like. An example humidity sensing component 213 may be or comprise a hygrometer, capacitive sensor, resistive sensor, thermal sensor and/or the like. In various embodiments, the humidity sensing component 213 is in electronic communication with controller component of the apparatus 200 such that it can exchange data (e.g., receive and transmit data) with a controller component of the apparatus 200. In some embodiments, the controller component of the apparatus 200 may process data (e.g., a humidity level indication) received from the humidity sensing component 213 in order to determine parameters for activating and deactivating the dehumidifier component 209 (e.g., a time period, a target temperature and/or the like).

As noted above, the apparatus 200 also comprises a dehumidifier component 209 disposed upstream with respect to the humidity sensing component 213 and the gas detecting component 205 along the gas flow channel 202. In various embodiments, the dehumidifier component 209 may comprise an arrangement of one or more components configured to extract, convey and expel a liquid from a gaseous substance in the gas flow channel 202.

As shown in FIG. 2, the dehumidifier component 209 may comprise a cooling element 211. In some embodiments, the cooling element 211 may be or comprise a semiconductor-based device, thermoelectric cooler (TEC), Peltier cooling module or solid-state device that uses the Peltier effect to create a heat flux at a junction of two different materials. An example cooling element 211 may comprise an n-type semiconductor and a p-type semiconductor parallel to one another (i.e., facing one another) with an interconnect therebetween. The cooling element 211 may be configured to decrease a temperature level in the gas flow channel 202, causing water vapor to condense on a surface of the dehumidifier component 209. As shown, the cooling element 211 may be located above/adjacent the gas flow channel 202 such that it is adjacent the flow path of the gaseous substance. Subsequent to the cooling element 211 causing water vapor to condense on a surface of the dehumidifier component 209, the water vapor may be conveyed through the water channel 215 and expelled from the apparatus 200 (e.g., via the gas outlet 203). In so doing, the water vapor does not continue to travel along the gas flow channel 202 together with the gaseous substance and make contact with various components of the apparatus 200 that are downstream with respect to the dehumidifier component 209 such as, for example, the humidity sensing component 213 and the gas detecting component 205. In various embodiments, the dehumidifier component 209 may be fixedly or removably coupled to the apparatus 200. For example, the dehumidifier component 209 may be removable in order to facilitate maintenance or replacement of components therein.

Additionally, as shown, the apparatus 200 may comprise a gas detecting component 205 disposed downstream along the gas flow channel 202 with respect to the dehumidifier component 209. If a gaseous substance flowing through the gas flow channel 202 is associated with a high humidity level (for example, as detected by the humidity sensing component 213), then the apparatus, such as the controller component may transmit a control indication to trigger activating the dehumidifier component 209 in order to decrease a temperature level in the gas flow channel 202 before the gaseous substance reaches the gas detecting component 307. The gas detecting component may generate measurements indicating a concentration level of a testing compound in a testing gaseous substance.

In some embodiments, the gas detecting component 205 may be a photoionization detector. As discussed above with reference to the example provided in FIG. 1, gas detecting component 205 is configured to detect VOCs within a gaseous substance when at least a portion of the gaseous substance is incident thereon (such as within a window member of an example photoionization detector). However, other types of apparatuses and gas detection components may be provided.

Figure 3:
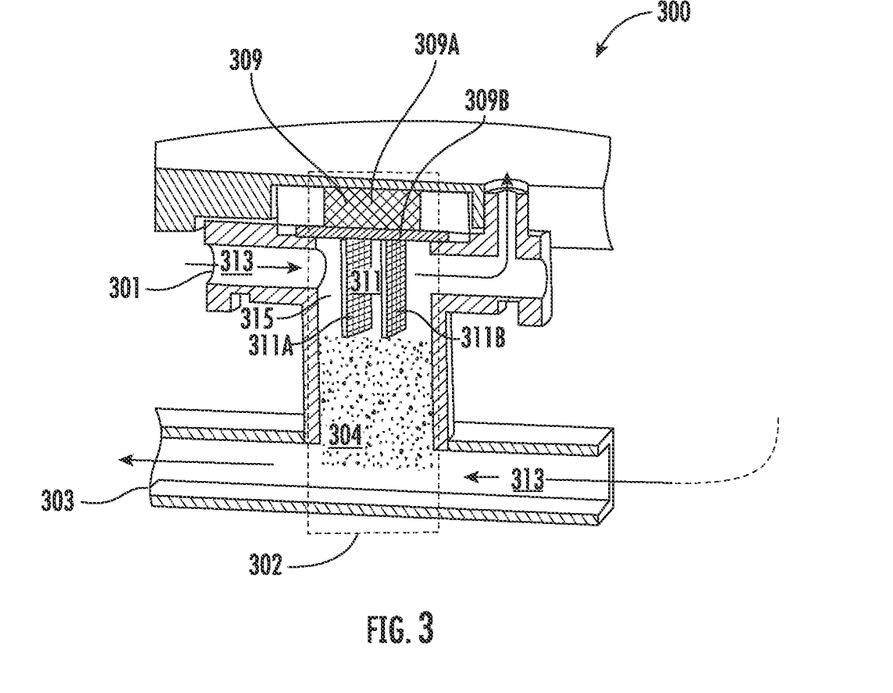
FIG. 3 illustrates a cross section view of an example portion of an apparatus in accordance with various embodiments of the present disclosure.

Referring now to FIG. 3, a cross section view of an example portion of an apparatus 300 in accordance with various embodiments of the present disclosure is provided. In particular, FIG. 3 illustrates example components associated with an example dehumidifier component 302. In the example shown in FIG. 3, the dehumidifier component 302 comprises a cooling element 309, a filter component 311 comprising metal net structures 311A and 311B and a water absorbing material 304.

As shown, the apparatus 300 comprises a gas flow channel 313 defining a passageway through which a gaseous substance may enter, flow through and be expelled from the apparatus 300. As shown, the gas flow channel 313 comprises a pipe, conduit, tubular structure and/or the like.

During operations, the gaseous substance may enter the apparatus 300 through a gas inlet 301 and is conveyed along the gas flow channel 313 in a direction due to air flow generated by a pump. The gaseous substance may be conveyed to the dehumidifier component 302. Subsequent to flowing past the dehumidifier component 302, the gaseous substance is conveyed to another portion of the apparatus 300, such as to the location of the humidity detecting component and/or gas detecting component (e.g., photoionization detector). Subsequently, the gaseous substance may be conveyed further along the gas flow channel 313 before being expelled from the apparatus through the gas outlet 303 where the gas flow channel 313 terminates.

As shown in FIG. 3, the dehumidifier component 302 may comprise a filter component. As shown, the filter component 311 comprises two metal net structures 311A and 311B. While FIG. 3 provides an example of a filter component 311 that comprises an arrangement of two metal net structures, it is noted that the scope of the present disclosure is not limited to the example shown in FIG. 3. In some examples, an example filter component 311 may comprise one or more additional and/or alternative elements, and/or may be structured/positioned differently than those illustrated in FIG. 3. For example, an example filter component 311 may comprise one metal net structure. Additionally, or alternatively, an example filter component 311 may comprise more than two metal net structures.

As depicted, the example metal net structures 311A and 311B are in contact with a bottom side of the cooling element 309 (i.e., in contact with a lower cooling side 309B of the cooling element 309). Additionally, the metal net structures 311A and 311B are arranged perpendicular to the direction of air flow through the gas flow channel 313 and spaced apart from one another. When a voltage is applied across the cooling element 309, a flow of direct current across the junction of the semiconductors creates a corresponding temperature difference between an upper heating side 309A of the cooling element 309 and a lower cooling side 309B of the cooling element 309. In some embodiments, the lower cooling side 309B is disposed on an inner surface of the gas flow channel 313 and in contact with the gaseous substance flowing through the gas flow channel 313, resulting in a decrease in a temperature level in the gas flow channel 313 and causing water vapor to condense on a surface of the filter component 311 (e.g., one or more surfaces of the metal net structures 311A and 311B). At least a portion of the dehumidifier component 302 (for example, as shown, the filter component 311) may intersect a portion of the gas flow channel 313. For example, the filter component 311 of the dehumidifier component 302 is in the path of the gaseous substance flowing through the gas flow channel 313 of the apparatus 300. In the example shown in FIG. 3, the lower cooling side 309B of the cooling element 309 is disposed directly above the metal net structures 311A and 311B of the filter component 311 which intersects the gas flow channel 313 of the apparatus 300. Thus, as the gaseous substance flows past the metal net structures 311A and 311B, the gaseous substance is cooled causing water vapor to condense onto the surface(s) of the metal net structures 311A and 311B.

As described above, at least a portion of the dehumidifier component 302 (for example, the water absorbing material 304) may be arranged, contained, or disposed within a water channel 315. In some embodiments, the water channel 315 may be in a perpendicular arrangement with the gas flow channel 313. In some embodiments, the water channel 315 comprises a pipe, conduit, tubular structure and/or the like. In some embodiments, the water channel 315 defines a passageway through which extracted water vapor can be expelled from the apparatus 300 in order to bypass some of the components of the apparatus 300 (e.g., humidity sensing component and gas detecting component). In some embodiments, as shown, the water channel 315 is a vertical channel or passage perpendicularly intersecting the gas flow channel 313 at a first location adjacent the gas inlet 301 and at second location adjacent the gas outlet 303, and connecting the first location adjacent the gas inlet 301 and the second location adjacent the gas outlet 303, such that the water channel 315 defines a water passage for transporting a liquid substance (e.g., water vapor) from the first location adjacent the gas inlet 301 to the second location adjacent the gas outlet 303. Accordingly, the water channel 315 prevents the water vapor from flowing along the entire flow path of the gas flow channel 313 through the apparatus.

As noted above, in some embodiments, the dehumidifier component 302 comprises a water absorbing material 304 at a bottom end of the water channel 315 and defining a bottom end of the dehumidifier component 302. As shown, in some embodiments, the water absorbing material 304 completely occupies a space/cavity at the bottom end of the water channel 315. Additionally, the water absorbing material 304 is arranged underneath and in contact with the filter component 311 such that gravity causes the water vapor trapped/collected by the filter component 311 to travel downwards where it is absorbed by the water absorbing material 304. The water absorbing material 304 may be or comprise any material suitable for absorbing a liquid substance such as, for example, without limitation, foam, fabric, textile and/or the like. In various embodiments, the water absorbing material may be configured to hold up to at least ten times its weight. Thus, liquid substance (e.g., water vapor) that is extracted by the filter component 311 is conveyed downward though the water channel 315 bypassing other components of the apparatus 300. Additionally, gravity may cause the water vapor to descend via the water channel 315 where it is absorbed by the water absorbing material 304 at the bottom of the water channel 315. In some embodiments, the descended water vapor may be expelled from the apparatus 300 via the gas outlet 303 as a result of output air generated by the pump forcing the water vapor to exit the apparatus 300.

While FIG. 3 provides an example of an example dehumidifier component 302, it is noted that the scope of the present disclosure is not limited to the example shown in FIG. 3. In some examples, an example dehumidifier component may comprise one or more additional and/or alternative elements, and/or may be structured/positioned differently than those illustrated in FIG. 3.

Figure 4:
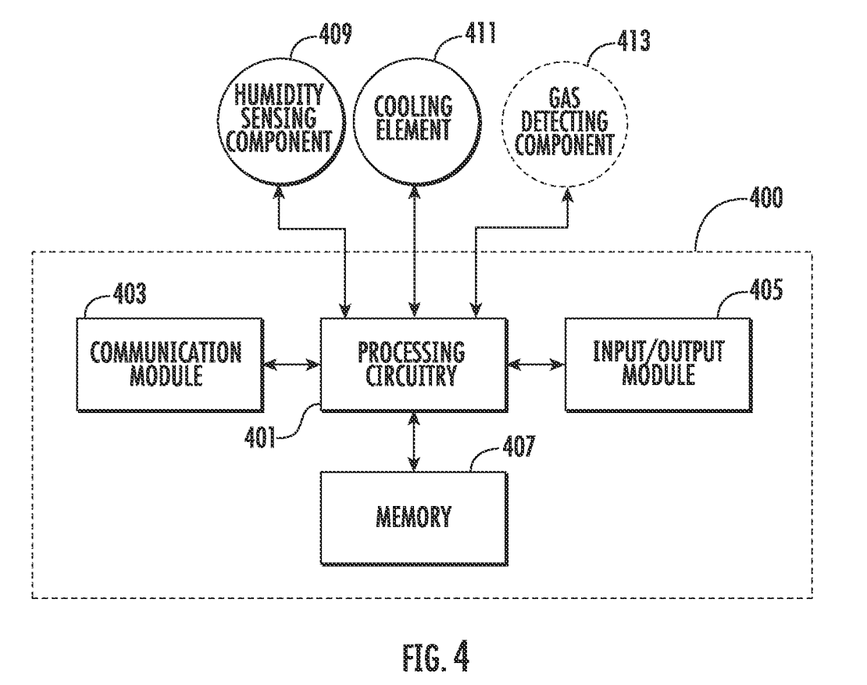
FIG. 4 illustrates an example controller component in electronic communication with various other components of an example apparatus in accordance with various embodiments of the present disclosure.

Referring now to FIG. 4, a schematic diagram depicting an example controller component 400 of an example apparatus in electronic communication with various other components in accordance with various embodiments of the present disclosure. As shown, the controller component 400 comprises processing circuitry 401, a communication module 403, input/output module 405, a memory 407 and/or other components configured to perform various operations, procedures, functions or the like described herein.

As shown, the controller component 400 (such as the processing circuitry 401, communication module 403, input/output module 405 and memory 407) is electrically coupled to and/or in electronic communication with a humidity sensing component 409, a dehumidifier component (e.g., a cooling element 411 of the dehumidifier component) and a gas detection component 413. As depicted, each of the humidity sensing component 409, the cooling element 411 of the dehumidifier component and the gas detection component 413 may exchange (e.g., transmit and receive) data with the processing circuitry 401 of the controller component 400.

The processing circuitry 401 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 401 may comprise one or more processors. In one exemplary embodiment, the processing circuitry 401 is configured to execute instructions stored in the memory 407 or otherwise accessible by the processing circuitry 401. When executed by the processing circuitry 401, these instructions may enable the controller 400 to execute one or a plurality of the functions as described herein. No matter whether it is configured by hardware, firmware/software methods, or a combination thereof, the processing circuitry 401 may comprise entities capable of executing operations according to the embodiments of the present invention when correspondingly configured. Therefore, for example, when the processing circuitry 401 is implemented as an ASIC, an FPGA, or the like, the processing circuitry 401 may comprise specially configured hardware for implementing one or a plurality of operations described herein. Alternatively, as another example, when the processing circuitry 401 is implemented as an actuator of instructions (such as those that may be stored in the memory 407), the instructions may specifically configure the processing circuitry 401 to execute one or a plurality of algorithms and operations described herein, such as those discussed with reference to FIG. 5.

The memory 407 may comprise, for example, a volatile memory, a non-volatile memory, or a certain combination thereof. Although illustrated as a single memory in FIG. 4, the memory 407 may comprise a plurality of memory components. In various embodiments, the memory 407 may comprise, for example, a hard disk drive, a random access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 407 may be configured to store information, data, application programs, instructions, and etc., so that the controller 400 can execute various functions according to the embodiments of the present disclosure. For example, in at least some embodiments, the memory 407 is configured to cache input data for processing by the processing circuitry 401. Additionally or alternatively, in at least some embodiments, the memory 407 is configured to store program instructions for execution by the processing circuitry 401. The memory 407 may store information in the form of static and/or dynamic information. When the functions are executed, the stored information may be stored and/or used by the controller 400.

The communication module 403 may be implemented as any apparatus included in a circuit, hardware, a computer program product or a combination thereof, which is configured to receive and/or transmit data from/to another component or apparatus. The computer program product comprises computer-readable program instructions stored on a computer-readable medium (for example, the memory 407) and executed by a controller 400 (for example, the processing circuitry 401). In some embodiments, the communication module 403 (as with other components discussed herein) may be at least partially implemented as the processing circuitry 401 or otherwise controlled by the processing circuitry 401. In this regard, the communication module 403 may communicate with the processing circuitry 401, for example, through a bus. The communication module 403 may comprise, for example, antennas, transmitters, receivers, transceivers, network interface cards and/or supporting hardware and/or firmware/software, and is used for establishing communication with another apparatus. The communication module 403 may be configured to receive and/or transmit any data that may be stored by the memory 407 by using any protocol that can be used for communication between apparatuses. The communication module 403 may additionally or alternatively communicate with the memory 407, the input/output module 405 and/or any other component of the controller 400, for example, through a bus.

In some embodiments, the controller 400 may comprise an input/output module 405. The input/output module 405 may communicate with the processing circuitry 401 to receive instructions input by the user and/or to provide audible, visual, mechanical or other outputs to the user. Therefore, the input/output module 405 may comprise supporting devices, such as a keyboard, a mouse, a display, a touch screen display, and/or other input/output mechanisms. Alternatively, at least some aspects of the input/output module 405 may be implemented on a device used by the user to communicate with the controller 400. The input/output module 405 may communicate with the memory 407, the communication module 403 and/or any other component, for example, through a bus. One or a plurality of input/output modules and/or other components may be included in the controller 400.

For example, the humidity sensing component 409 may be similar to humidity sensing component 213 described above with regard to FIG. 2. For example, humidity sensing component 409 may generate a humidity level indication and transmit the humidity level indication to the processing circuitry 401. In some embodiments, cooling element 411 may be similar to cooling element 309 described above with regard to FIG. 3. For example, cooling element 411 may receive a first control indication from the processing circuitry 401 triggering activation of the cooling element 411. For example, cooling element 411 may receive a second control indication from the processing circuitry 401 triggering deactivation of the cooling element 411. In some embodiments, gas detection component 413 may be similar to gas detecting component 205 described above with regard to FIG. 2. For example, gas detection component 413 may generate measurements indicating a concentration level of a testing compound in a testing gaseous substance and transmit a concentration level indication to the processing circuitry 401.

Figure 5:
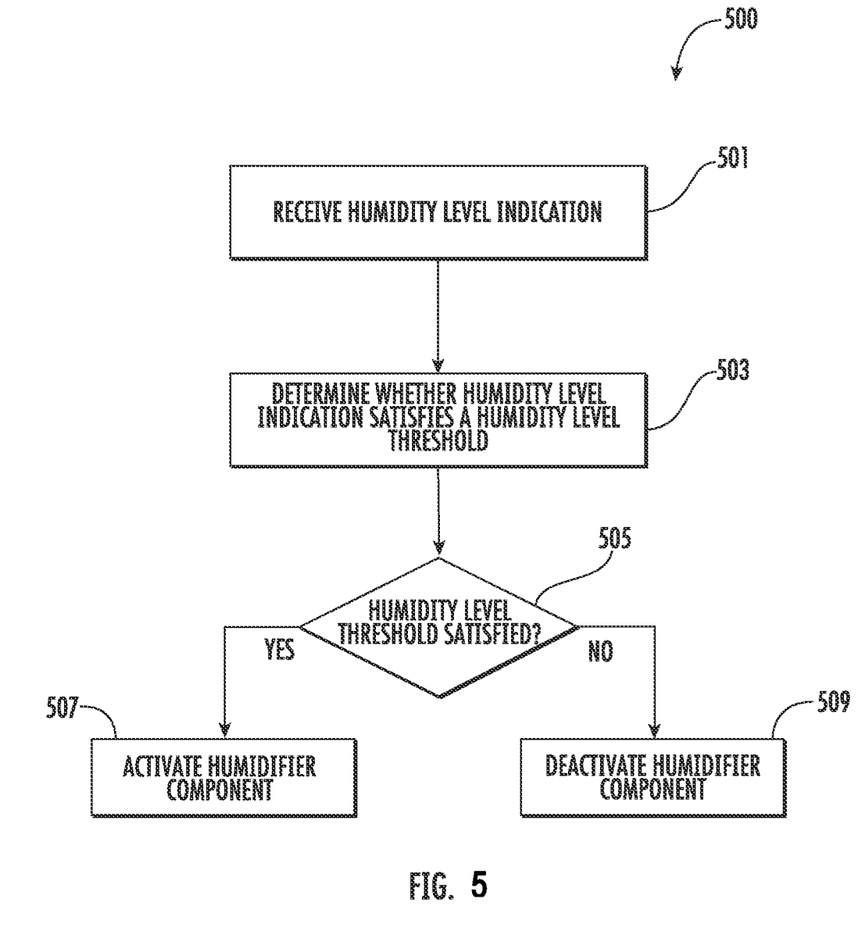
FIG. 5 is a flowchart diagram illustrating example operations in accordance with various embodiments of the present disclosure.

Referring now to FIG. 5, a flowchart diagram illustrating example operations 500 in accordance with various embodiments of the present disclosure is provided.

In some examples, the method 500 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example apparatus, such as, but not limited to, a humidity sensing component, a dehumidifier component, a gas detecting, a memory (such as, for example, random access memory (RAM) for storing computer program instructions), and/or a display circuitry (for rendering readings on a display).

In some examples, one or more of the procedures described in FIG. 5 may be embodied by computer program instructions, which may be stored by a memory (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram step/operation(s). Further, the system may comprise one or more other circuitries. Various circuitries of the system may be electronically coupled between and/or among each other to transmit and/or receive energy, data and/or information.

In some examples, embodiments may take the form of a computer program product on a non-transitory computer-readable storage medium storing computer-readable program instruction (e.g., computer software). Any suitable computer-readable storage medium may be utilized, including non-transitory hard disks, CD-ROMs, flash memory, optical storage devices, or magnetic storage devices.

The example method 500 begins at step/operation 501. At step/operation 501, a processing circuitry (such as, but not limited to, the processing circuitry 401 of the controller component 400 illustrated in connection with FIG. 4, discussed above) receives a humidity level indication associated with a gaseous substance in the gas flow channel. In some embodiments, a humidity sensing component (such as, but not limited to, the humidity sensing component 409 illustrated in connection with FIG. 4) may transmit a humidity level indication associated with a gaseous substance in the gas flow channel to the processing circuitry.

Subsequent to step/operation 501, the example method 500 proceeds to step/operation 503. At step/operation 503, the processing circuitry determines whether the humidity level indication satisfies a humidity level threshold.

As noted above, in some embodiments, the humidity level threshold may be a measure of humidity (e.g., AH and/or RH) associated with a gaseous substance in the gas flow channel at which the apparatus can operate at a reduced or acceptable error tolerance. The humidity level threshold may be a predetermined and/or configurable threshold (e.g., a value between 40% and 60% RH). In some embodiments, an operator of the apparatus may select the humidity level threshold prior to operating the apparatus.

In some embodiments, the processing circuitry may determine that the humidity level indication does not satisfy a humidity level threshold if the humidity level indicated by the humidity level indication is equal to or below the humidity level threshold. For example, when the humidity level indication does not satisfy the humidity level threshold, it may indicate that the apparatus may operate with a reduced likelihood of error and/or increased responsiveness. As an example, if the humidity level threshold is 60% RH and the humidity level indication indicates that the humidity level is 56% RH, then the humidity level indication does not satisfy the humidity level threshold because it is below the humidity level threshold. In another example, if the humidity level threshold is 70% RH and the humidity level indication indicates that the humidity level is 70% RH, then the humidity level indication does not satisfy the humidity level threshold because it is equal to the humidity level threshold.

In some embodiments, the processing circuitry may determine that the humidity level indication satisfies a humidity level threshold if the humidity level indicated by the humidity level indication is above the humidity level threshold. For example, when the humidity level indication satisfies the humidity level threshold, it may indicate that the apparatus may operate with an increased likelihood of error and/or decreased responsiveness. By way of example, if the humidity level threshold is 60% RH and the humidity level indication indicates that the humidity level is 70% RH, then the humidity level indication satisfies the humidity level threshold because it is above the humidity level threshold. As another example, if the humidity level threshold is 75% RH and the humidity level indication indicates that the humidity level is 95% RH, then the humidity level indication satisfies the humidity level threshold because it is above the humidity level threshold.

Subsequent to step/operation 503, the method 500 proceeds to step/operation 505. At step/operation 505, if the processing circuitry determines that the humidity level threshold is satisfied, then the method 500 proceeds step/operation 507. As another example, if the humidity level threshold is 70% RH and the humidity level indication indicates that the humidity level is 95% RH, then the humidity level indication satisfies the humidity level threshold because it is above the humidity level threshold and method 500 will proceed to step/operation 507.

Subsequent to step/operation 505, at step/operation 507, in response to determining that the humidity level indication satisfies the humidity level threshold, the processing circuitry activates the dehumidifier component by transmitting a first control indication to the cooling element (such as, but not limited to, the cooling element 411 illustrated in connection with FIG. 4, discussed above). Activating the dehumidifier component may comprise causing a switch connected to a power supply of the cooling element to be turned on in response to receiving the control indication. The cooling element may be configured to decrease a temperature level in the gas flow channel, causing water vapor to condense on a surface of the filter component (e.g., a metal net structure). Additionally, as noted above, as a result of the output air of a pump, water vapor may be expelled from the apparatus through a water channel (for example, via the water channel 315 illustrated and described above in connection with FIG. 3) housing at least a portion of the dehumidifier component (for example, but not limited to, the water absorbing material 304 illustrated and described above in connection with FIG. 3).

Returning to step/operation 505, if the processing circuitry determines that the humidity level indicated by the humidity level indication does not satisfy the humidity level threshold, such as by determining that the humidity level indication is equal to or less than a humidity level threshold, the method 500 proceeds to step/operation 509 instead. For example, if the humidity level threshold is 70% RH and the humidity level indication indicates that the humidity level is 66% RH, then the humidity level indication does not satisfy the humidity level threshold because it is below the humidity level threshold and method 500 will proceed to step/operation 509.

At step/operation 509, in response to determining that the humidity level indication does not satisfy the humidity level threshold, the processing circuitry deactivates the dehumidifier component by transmitting a second control indication to the cooling element (such as, but not limited to, the cooling element 411 illustrated in connection with FIG. 4, discussed above). Deactivating the dehumidifier component may consist of causing a switch connected to a power supply of the cooling element to be turned off in response to receiving the second control indication.

As described above, water vapor may interfere with the accuracy of readings obtained by the gas detecting component. As such, the processing circuitry may thus utilize a feedback loop to maintain optimal operating conditions for the gas detecting component by monitoring and responding to reduce the temperature in the gas flow chamber of the apparatus such that water vapor can be extracted and expelled from the apparatus and prevented from coming into contact with the gas detecting component (for example, but not limited to, the gas detecting component 205 illustrated and described above in connection with FIG. 2).

Figure 6:
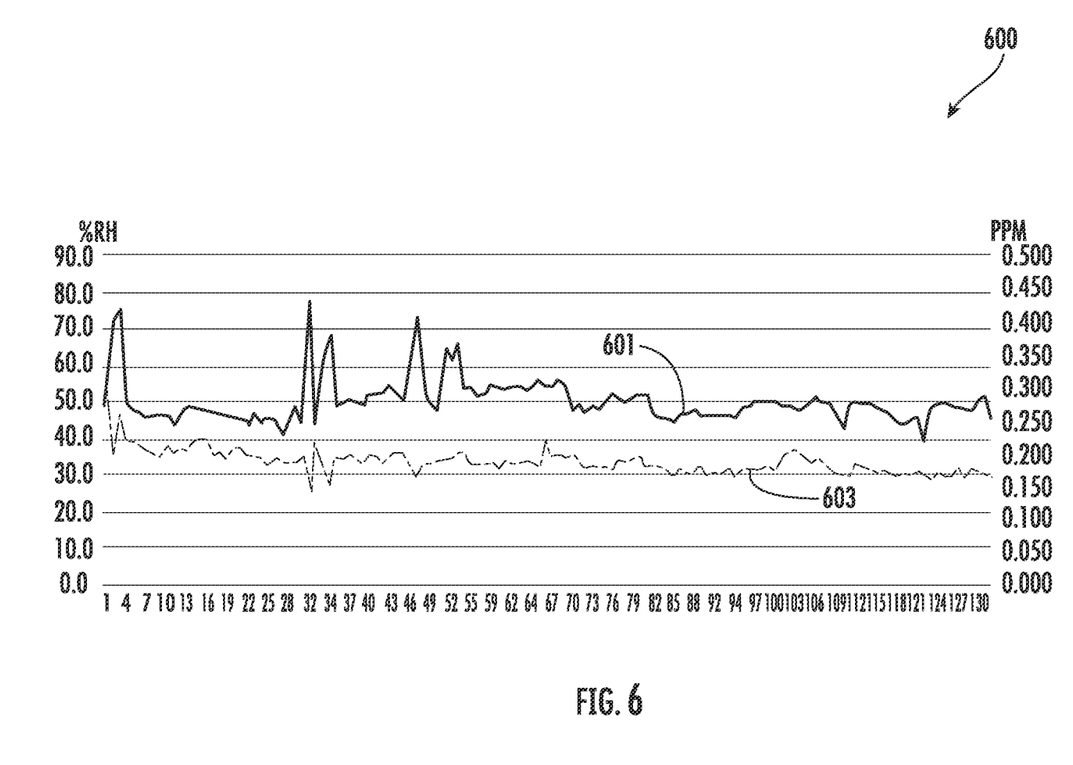
FIG. 6 illustrates a graph depicting example measurements.

Referring now to FIG. 6, a graph depicting example measurements is provided. As depicted in FIG. 6. the x-axis represents a plurality of instances in time. As depicted, the y-axis represents, for a first line of the graph, 601 humidity levels (RH). As depicted, the y-axis also represents, for a second line 603 of the graph, a concentration of a compound in a gaseous substance measured in parts per million (PPM).

As illustrated in FIG. 6, a plurality of measurements 603 of a compound in a gaseous substance (e.g., the same or similar gaseous substance) captured by a gas detector over time fluctuates. As further illustrated in FIG. 6, a detected relative humidity level 601 is captured for each of the plurality of measurements indicated in the second line 603 in the graph. As shown in FIG. 6, the detected relative humidity levels 601 correspond closely with (e.g., fluctuate with respect to) each respective measurement of the compound in the gaseous substance. Accordingly, FIG. 6 demonstrates that the relative humidity level affects the accuracy of measurements obtained by the gas detector.

Figure 7:
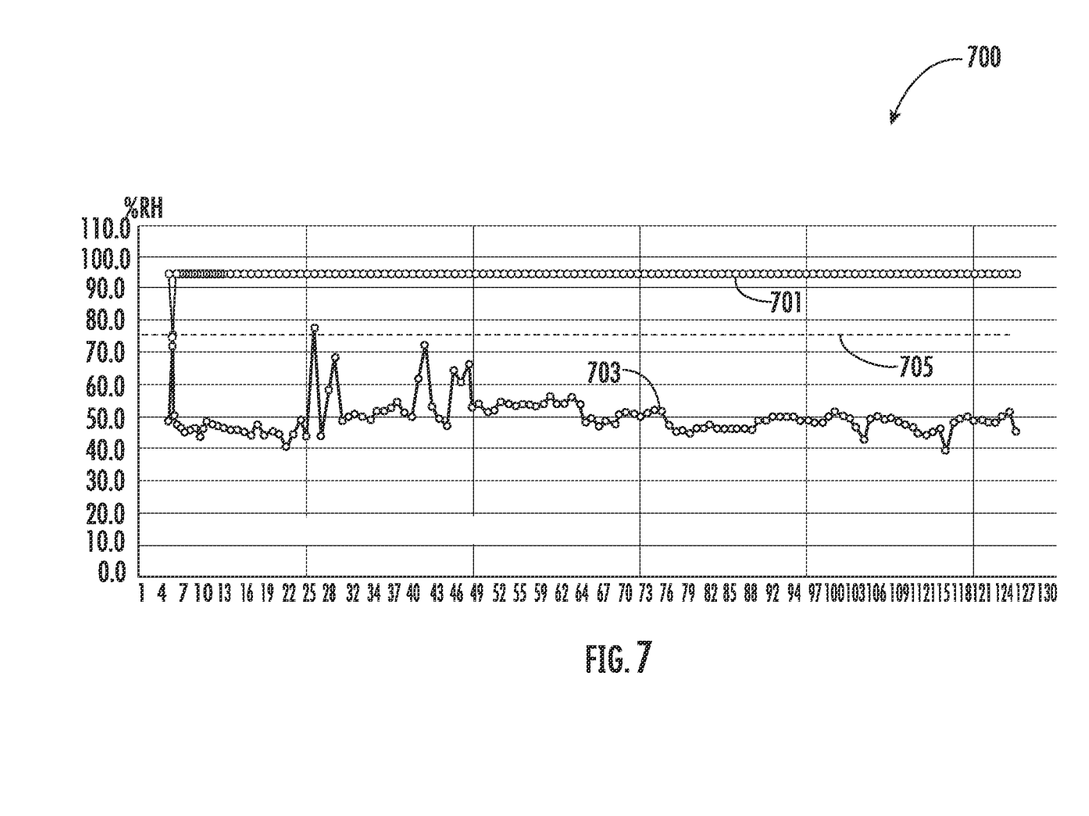
FIG. 7 illustrates a graph depicting example measurements associated with an example apparatus in accordance with various embodiments of the present disclosure.

Referring now to FIG. 7, a graph depicting example measurements of an example apparatus in accordance with various embodiments of the present disclosure is provided. As depicted in FIG. 7, the x-axis represents a plurality of instances in time. As depicted, the y-axis represents a humidity level measurement (RH) associated with a gaseous substance entering or within an example apparatus. As illustrated in FIG. 7, the first line 701 of the graph depicts a humidity level measurement associated with a gaseous substance entering the example apparatus (e.g., near the gas inlet) which is detected upon entry. A second line 703 of the graph depicts a humidity level measurement associated with the gaseous substance when it is adjacent the gas detecting component. FIG. 7 also indicates a humility level threshold 705 for the apparatus which is 75% RH.

As depicted in FIG. 7, the humidity level for a gaseous substance entering the apparatus (as plotted on the first line 701) is higher than the humidity level for the same gaseous substance when it is adjacent the gas detecting component (as plotted on the second line 703). Accordingly, as shown, the apparatus is able to reduce the amount of water vapor associated with a given gaseous substance. For example, as described above in relation to FIG. 4, by causing a cooling element 411 to be activated when a humidity level indication associated with a gaseous substance is above a humidity level threshold. As shown, in response to an input gaseous substance with a high humidity level of 95% RH, the apparatus is able to control and maintain a humidity level below the humidity level threshold 705 such that excess water vapor does not come in contact with a gas detecting component of the apparatus. Thus, the responsiveness of the apparatus is not adversely affected and accuracy of gas detection measurements can be maintained.

Many modifications and other embodiments of the present disclosure set forth herein will come to mind to one skilled in the art to which these embodiments pertain having the benefit of the teachings presented in the foregoing descriptions and the associated drawings. Therefore, it is to be understood that the disclosure are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. An apparatus comprising:
   a humidity sensing component configured to generate a humidity level indication associated with gaseous substance in a gas flow channel;
   a dehumidifier component disposed along the gas flow channel, wherein the dehumidifier component comprises a cooling element in contact with the gaseous substance in the gas flow channel;
   a gas detecting component disposed downstream with respect to the dehumidifier component along the gas flow channel; and
   a controller component in electronic communication with the humidity sensing component and the dehumidifier component,
   wherein the dehumidifier component further comprises a filter component disposed underneath the cooling element in the gas flow channel, wherein the gas flow channel and the filter component intersect at least a portion of a vertical water channel defining a passage through which water vapor is expelled from the apparatus without coming in contact with the humidity sensing component and the gas detecting component.

2. The apparatus of claim 1, wherein the controller component is configured to:
   receive the humidity level indication from the humidity sensing component;
   determine whether the humidity level indication satisfies a humidity level threshold; and
   in response to determining that the humidity level indication satisfies the humidity level threshold, transmit a first control indication to trigger activating the dehumidifier component.

3. The apparatus of claim 2, wherein the controller component is configured to:
   in response to determining that the humidity level indication does not satisfy the humidity level threshold, transmit a second control indication to trigger deactivating the dehumidifier component.

4. The apparatus according to claim 3, wherein the humidity level threshold is between 40% and 60% relative humidity.

5. The apparatus according to claim 1, wherein the gaseous substance in the gas flow channel comprises the water vapor, wherein, when activating the dehumidifier component, the controller component is configured to further:
   activate the cooling element, wherein the cooling element is configured to decrease a temperature level in the gas flow channel, causing the water vapor to condense on a surface of the filter component.

6. The apparatus according to claim 5, wherein the filter component comprises one or more metal net structures arranged within the gas flow channel, wherein the gaseous substance flows through the one or more metal net structures.

7. The apparatus according to claim 6, wherein the dehumidifier component further comprises a water absorbing material arranged underneath the filter component, wherein the water absorbing material is disposed in the vertical water channel and is configured to absorb a liquid substance from the surface of the filter component.

8. The apparatus according to claim 7, wherein the apparatus further comprises a pump, and wherein the water absorbing material is further configured to, in conjunction with output air of the pump, expel the water vapor from the apparatus.

9. The apparatus according to claim 8, wherein the water absorbing material comprises a foam or a textile.

10. A method comprising:
    receiving, by a controller component, a humidity level indication from a humidity sensing component, wherein the humidity level indication is associated with a gaseous substance in a gas flow channel;
    determining, by the controller component, whether the humidity level indication satisfies a humidity level threshold; and
    in response to determining that the humidity level indication satisfies the humidity level threshold, transmit a first control indication to trigger activating a dehumidifier component, wherein a cooling element is in contact with the gaseous substance in the gas flow channel,
    wherein a filter component is disposed underneath the cooling element in the gas flow channel, and wherein the gas flow channel and the filter component intersect at least a portion of a vertical water channel defining a passage through which water vapor is expelled from an apparatus without coming in contact with the humidity sensing component and a gas detecting component disposed downstream with respect to the dehumidifier component along the gas flow channel.

11. The method according to claim 10, further comprising:
    in response to determining that the humidity level indication does not satisfy the humidity level threshold, transmit a second control indication to trigger deactivating the dehumidifier component.

12. The method according to claim 11, wherein the humidity level threshold is between 40% and 60% relative humidity.

13. The method according to claim 10, wherein the gaseous substance in the gas flow channel comprises the water vapor, wherein, activating the dehumidifier component further comprises:
    activating the cooling element, wherein the cooling element is configured to decrease a temperature level in the gas flow channel, causing the water vapor to condense on a surface of the filter component.

14. The method according to claim 13, wherein the filter component comprises one or more metal net structures arranged within the gas flow channel, wherein the gaseous substance flows through the one or more metal net structures.

15. The method according to claim 14, wherein the dehumidifier component further comprises a water absorbing material arranged underneath the filter component, wherein the water absorbing material defines a bottom portion of the vertical water channel and is configured to absorb the water vapor from the surface of the filter component.

16. The method according to claim 15, wherein the water absorbing material is further configured to, in conjunction with output air of a pump, expel the water vapor from the apparatus.

* * * * *